(12) United States Patent
Geisz et al.

(10) Patent No.: US 11,433,190 B2
(45) Date of Patent: Sep. 6, 2022

(54) METHOD AND SYSTEM FOR CONTROLLING PRESSURIZATION OF A PATIENT CAVITY USING A PRESSURE SENSOR OF A MEDICAL APPLIANCE

(71) Applicant: Lexion Medical, LLC, St. Paul, MN (US)

(72) Inventors: Carl M. Geisz, Edina, MN (US); Rochelle M. Amann, West Saint Paul, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 483 days.

(21) Appl. No.: 16/206,284

(22) Filed: Nov. 30, 2018

(65) Prior Publication Data
US 2019/0091421 A1 Mar. 28, 2019

Related U.S. Application Data

(63) Continuation-in-part of application No. 15/610,026, filed on May 31, 2017, now Pat. No. 10,646,667.

(51) Int. Cl.
*A61M 13/00* (2006.01)
*A61M 39/02* (2006.01)
(Continued)

(52) U.S. Cl.
CPC ....... *A61M 13/003* (2013.01); *A61B 17/3474* (2013.01); *A61M 39/0247* (2013.01);
(Continued)

(58) Field of Classification Search
CPC ............ A61M 13/003; A61M 2205/16; A61M 2205/3344; A61M 2205/50; A61B 17/3474; A61B 2017/00022; G16H 10/60
See application file for complete search history.

(56) References Cited

U.S. PATENT DOCUMENTS 5,209,721 A     5/1993  Wilk
5,328,458 A *   7/1994  Sekino ................ A61M 13/003
                                                          604/23
(Continued)

FOREIGN PATENT DOCUMENTS

DE      4306629     9/1994
EP      1 109 486   5/2000
(Continued)

OTHER PUBLICATIONS

Extended European Search Report; Application No. 19212434.5-1122; Reference No. JL104444P.EPP; 8 pages, dated Apr. 21, 2020.
(Continued)

*Primary Examiner* — Bradley J Osinski
(74) *Attorney, Agent, or Firm* — Baker Botts, LLP (57) ABSTRACT

A method comprises positioning a medical appliance having a primary pressure sensor at or within a patient incision site and supplying an insufflation fluid to the patient cavity. The method further comprises measuring a pressure in the patient cavity by the primary pressure sensor and controlling the supply of insufflation fluid by an insufflator to the patient cavity based at least on the measured pressure. The method further comprises determining, by a processor associated with the insufflator, that the measured pressure may be inaccurate and, in response to determining that the measured pressure may be inaccurate, controlling, by the insufflator, the supply of the insufflation fluid to the patient cavity based at least on a pressure measured by a backup pressure sensor.

20 Claims, 4 Drawing Sheets

(51) Int. Cl.
  *A61B 17/34* (2006.01)
  *A61M 16/00* (2006.01)
  *A61B 90/00* (2016.01)

(52) U.S. Cl.
  CPC ............ *A61B 2090/064* (2016.02); *A61M 2016/0027* (2013.01); *A61M 2039/0264* (2013.01); *A61M 2039/0279* (2013.01); *A61M 2205/16* (2013.01); *A61M 2205/3344* (2013.01); *A61M 2205/3358* (2013.01); *A61M 2205/3569* (2013.01); *A61M 2205/3592* (2013.01); *A61M 2205/50* (2013.01); *A61M 2205/502* (2013.01)

(56) References Cited

U.S. PATENT DOCUMENTS

| | | | |
|---|---|---|---|
| 5,389,077 | A | 2/1995 | Melinyshyn |
| 5,427,114 | A | 6/1995 | Colliver |
| 5,591,344 | A | 1/1997 | Kenley et al. |
| 5,676,155 | A | 10/1997 | Novak et al. |
| 6,295,877 | B1 | 10/2001 | Aboul-Hosn |
| 6,299,592 | B1 | 10/2001 | Zander |
| 6,905,489 | B2 | 6/2005 | Mantell |
| 7,285,112 | B2 | 10/2007 | Stubbs |
| 7,722,558 | B2 | 5/2010 | Ott |
| 8,216,189 | B2 | 7/2012 | Stubbs |
| 8,235,940 | B2 | 8/2012 | Davis |
| 8,715,219 | B2 | 5/2014 | Stearns |
| 9,138,549 | B2 | 9/2015 | Pagel |
| 2004/0102733 | A1 | 5/2004 | Naimark |
| 2005/0115043 | A1 | 6/2005 | Maeshima |
| 2008/0004681 | A1* | 1/2008 | Marshall ............ A61N 1/056 607/116 |
| 2009/0270794 | A1 | 10/2009 | Mantell |
| 2010/0078017 | A1 | 4/2010 | Andrieux et al. |
| 2012/0184897 | A1 | 7/2012 | Poll |
| 2015/0290403 | A1* | 10/2015 | Torisawa ............ A61B 1/00131 604/26 |
| 2016/0184496 | A1 | 6/2016 | Jaecklein et al. |
| 2018/0103977 | A1 | 4/2018 | Geisz et al. |

FOREIGN PATENT DOCUMENTS

| | | |
|---|---|---|
| EP | 2 825 840 | 9/2013 |
| EP | 3 409 222 A1 | 5/2018 |
| WO | WO2013011398 | 1/2013 |
| WO | WO 2018/044863 | 3/2018 |

OTHER PUBLICATIONS

Extended European Search Report re: Application No. 18175165.2-1113; 11 pages, dated Sep. 28, 2018.

* cited by examiner

METHOD AND SYSTEM FOR CONTROLLING PRESSURIZATION OF A PATIENT CAVITY USING A PRESSURE SENSOR OF A MEDICAL APPLIANCE

CROSS REFERENCE

This application is a continuation-in-part of U.S. application Ser. No. 15/610,026, filed May 31, 2017, and entitled "Method and System for Controlling Pressurization of a Patient Cavity Using a Pressure Sensor in a Trocar," which is hereby incorporated by reference herein.

TECHNICAL FIELD OF THE INVENTION

The present invention disclosure relates generally to medical procedures and more particularly to a method and system for controlling pressurization of a patient cavity using a pressure sensor of a medical appliance.

BACKGROUND OF THE INVENTION

Laparoscopic surgery is a standard procedure in hospitals. Abdominal and chest cavity operations are being performed with instruments inserted through small incisions into interior portions of the body. Such laparoscopic procedures are now considered the treatment of choice for operations such as the removal of the gall bladder, spleen, adrenal glands, uterus, and ovaries. These laparoscopic procedures are accomplished via access through a device typically known as a trocar. A trocar facilitates the introduction of laparoscopic instruments into the abdomen or chest of the body. These instruments are typically introduced into regions under fluid pressure. This fluid may be a gas, referred to herein as an insufflation gas.

Providing an insufflation gas into a body cavity is referred to as insufflation. Currently, insufflation is performed by providing a regulated pressurized insufflation gas to the peritoneal cavity via a cannula of the trocar. This insufflation gas, typically carbon dioxide, is supplied to a connection on the trocar tube by a flexible hose attached thereto. The medical instrument going through the innermost tube of the trocar should be sealed relative to the trocar so the insufflation gas will not escape from the patient.

A physician can use a trocar device to introduce different types of instruments into a patient. In order to reduce incisions into the body, typically the insufflation gas is delivered into a body cavity during specific medical procedures or treatment is done via a trocar that also allows insertion of an instrument via the innermost tube of the trocar. The purpose of using such a device is to inflate or distend the body cavity to (1) allow the surgeon to explore the area in which the surgery will be performed and (2) provide a view of the site to be treated or observed.

Insufflation is used in many common procedures including endoscopic surgical procedures, laparoscopic procedures performed on the abdominal cavity and orthoscopic procedures performed on the chest cavity. Additional medical access devices (e.g., trocars) can be used during the same surgical procedure to remove surgical smoke from the patient cavity or to continuously measure pressure within the body cavity.

SUMMARY OF THE INVENTION

According to one embodiment, a method includes positioning a medical appliance having a primary pressure sensor at or within a patient incision site and supplying an insufflation fluid to the patient cavity. The method further includes measuring a pressure in the patient cavity by the primary pressure sensor and controlling the supply of insufflation fluid by an insufflator to the patient cavity based at least on the measured pressure. The method further includes determining, by a processor associated with the insufflator, that the measured pressure may be inaccurate and, in response to determining that the measured pressure may be inaccurate, controlling, by the insufflator, the supply of the insufflation fluid to the patient cavity based at least on a pressure measured by a backup pressure sensor.

The teachings of the disclosure provide one or more technical advantages. Embodiments of the disclosure may have none, some, or all of these advantages. For example, in some embodiments, a method allows for continuous monitoring of pressure associated with a patient cavity even in the event of a pressure sensor failure. This allows safe completion of a surgical procedure without subjecting the patient to potential harm associated with deactivation of an associated insufflator. Further, providing a pressure sensor in conjunction with a medical access device nearer the patient cavity provides better pressure sensing and more stable control and does not require stopping the associated surgical procedure to measure pressure according to certain standard techniques.

Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE INVENTION

The present disclosure relates to a method for controlling pressurization of a patient cavity. The teachings of the disclosure recognize that more accurate control of such pressurization can occur by measuring the pressure in a patient cavity directly through use of a pressure sensor located on or associated with a trocar such that the pressure sensor is in direct contact with the gas region in the patient cavity but that in some instances such pressure sensors can be damaged and provide erroneous data. As such, it can be desirable to monitor such pressure measurements, and when the data appear faulty, switch control of such pressurization to be based on a secondary or back up measure of pressure within the pressure cavity. In some embodiments, a backup pressure sensor located in or on the insufflator is used to provide such a backup pressure measurement, and in some embodiments a backup pressure sensor is located in, on, or through the trocar.

Example embodiments are best understood by referring to FIGS. 1 through 3B of the drawings and the description below, like numerals being used for like and corresponding parts of the various drawings.

Figure 1:
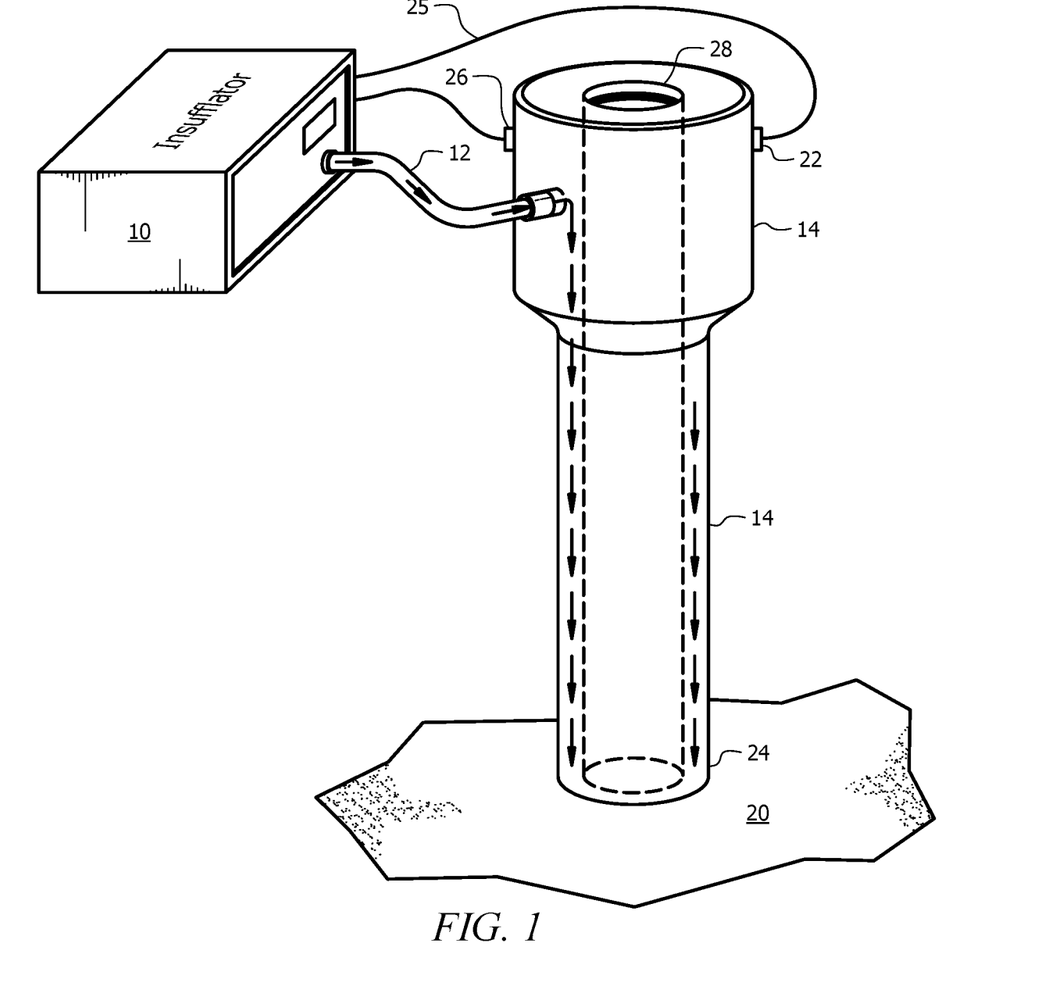
FIG. 1 is a schematic diagram showing the distal end of a trocar having an associated pressure sensor, the distal end placed in the abdominal cavity of a patient.

FIG. 1 is a schematic diagram showing the distal end 24 of a trocar 14 placed in the abdominal cavity 20 of a patient. In general, an insufflator 10 supplies insufflation gas through conduit 12 and trocar 14 to patient cavity 20. Trocar 14 allows insertion of a surgical instrument 28 into patient cavity 20.

Trocar 14 has a primary pressure sensor 22 on or associated with the trocar 14. The location can be anywhere in, on, or through trocar 14 or associated with trocar 14; however, as described in greater detail below, in one embodiment primary pressure sensor 22 is located on the exterior of trocar 14 such that changes of pressure within trocar 14 due to supply of insufflation gas to patient cavity 20 do not affect the pressure measured by primary pressure sensor 22. In some embodiments, primary pressure sensor 22 is an absolute pressure sensor that can measure pressure in patient cavity 20 (if disposed within patient cavity 20) or in the room in which the associated operation is taking place.

Primary pressure sensor 22 is coupled to insufflator through any suitable technique, including a wired connection 25 or a wireless connection. Primary pressure sensor 22 supplies pressure data to insufflator 10. Insufflator 10 uses this pressure data to control the supply on insufflation gas by insufflator 10. In particular embodiments, this may include determining the change in height of trocar 14 relative to changes in cavity pressure and thus the resulting change in height of patient cavity 20, as described in greater detail in co-pending application Ser. No. 15/293,013 entitled Method and System for Controlling Pressurization of a Patient Cavity Using Cavity Distension Measured by a Pressure Sensor of a Trocar incorporated herein by reference. Additional details of certain portions of FIG. 1 are described below.

Insufflator 10 may be any suitable source of insufflation gas at any suitable pressure and may include a pressurized gas source. Insufflator may adjust the supply of insufflation gas to patient cavity 20 by adjusting the pressure and/or the volume of insufflation gas supplied to patient cavity 20. Insufflator may include appropriate hardware and/or software for processing signals indicative of pressures measured by primary pressure sensor 22 and processing such signals to convert them into useful information, such as converting them into pressures, heights, and/or other data that can be used control the flow of insufflation gas to patient cavity 20, and further for processing such data to determine a desired pressure and/or volume of insufflation gas supplied to patient cavity 20 and for effecting such delivery.

Conduit 12 may be any suitable conduit for providing an insufflation gas to a portion of a trocar. An example of conduit 12 includes flexible PVC tubing. The insufflation gas may be any suitable gas used for insufflation purposes. In one example, insufflation case is carbon dioxide.

Trocar 14 may be any suitable trocar through which insufflation gas may be supplied to a patient cavity. Examples of one or more trocars are provided in U.S. Pat. No. 8,715,219 (the '219 patent), U.S. Pat. No. 7,285,112 (the '112 patent), and U.S. Pat. No. 8,216,189 (the '189 patent), which are hereby incorporated by reference as if fully set forth herein. Trocar 14 may be have a single lumen or may be formed with an inner tubular lumen and an outer tubular lumen such that insufflation gas may be supplied through one of the lumens but not the other. Further, any of the lumens may be divided into multiple, separate chambers, such that gas in one chamber does not enter the other chamber. Examples of the above multiple lumens and multiple chambered trocars are described in U.S. application Ser. No. 14/792,873, entitled "Method and System for Gas Maintenance to a Body Cavity Using a Trocar," which is hereby incorporated by reference. Trocar 14 may be open or closed at the distal end 24, as the application of the trocar would allow.

Primary pressure sensor 22 may be any sensor capable of sensing pressure or a change in pressure. Primary pressure sensor 22 may measure absolute pressure or a pressure relative to some other pressure. In some embodiments, primary pressure sensor 22 is an absolute sensor that can measure pressure in patient cavity 20 (if disposed within patient cavity 20) or in the room in which the associated operation is taking place. In particular embodiments, primary pressure sensor 22 can measure absolute barometric pressures with an accuracy of less than 1 Pascal pressure and therefore have the ability to measure the relative changes in altitude of close to one inch. Such pressure sensors are readily available in the marketplace.

Figure 2A:
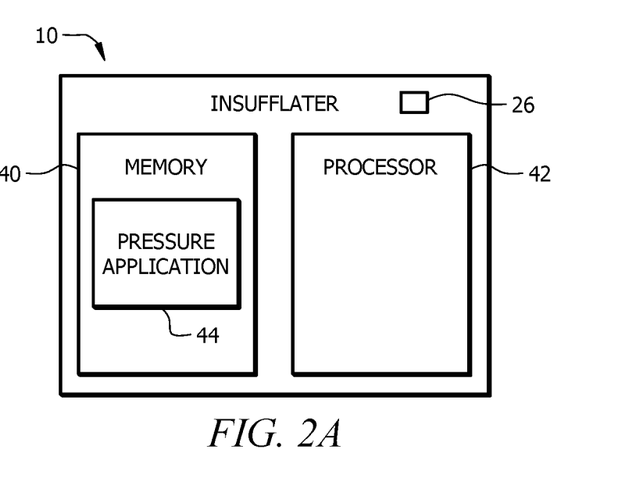
FIGS. 2A and 2B are block diagrams illustrating additional details of components of the system of FIG. 1 that may be used to effect pressure determination and resulting actions.
Figure 2B:
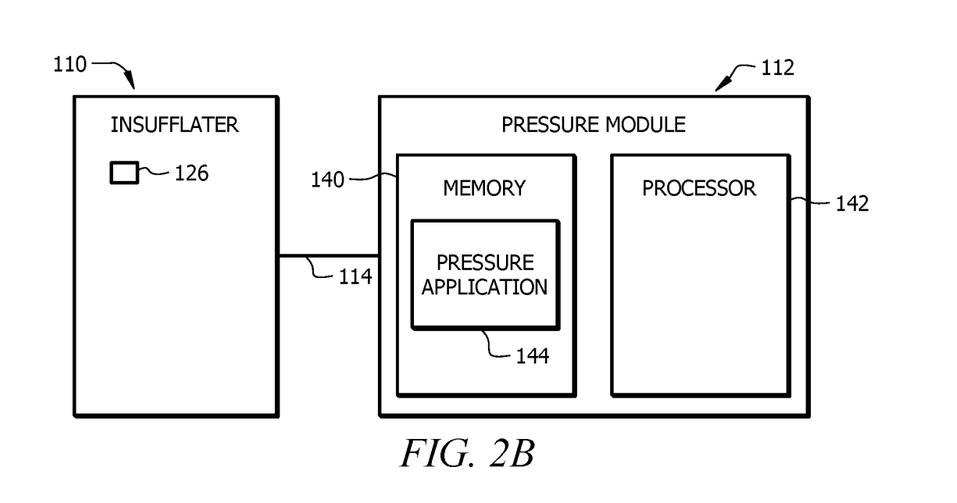

FIGS. 2A and 2B are block diagrams illustrating additional details of components of the system of FIGURE that may be used to effect pressure measurement and resulting insufflator control. FIG. 2A illustrates additional details of insufflator 10, according to one embodiment. In this embodiment, insufflator 10 includes a memory 40 and a processor 42 communicatively coupled to the memory 40. Memory 40 stores a pressure application 44, which may include logic for effecting pressure and altitude determination as described with respect to the other FIGURES as well as control of the supply of insufflation gas to patient cavity 20. According to the teaching of the disclosure, a backup pressure sensor 26 is provided. In one embodiment, insufflator 10 includes a backup pressure sensor 26. Backup pressure sensor 26 may be used to measure pressure associated with trocar 14 in the event or problems associated with primary pressure sensor 22, as described in greater detail below in conjunction with FIG. 3. In another embodiment, backup pressure sensor 26 is provided on trocar 14, as illustrated in FIG. 1. The teachings of the disclosure recognize that primary pressure sensor 22 may experience problems due to being located a larger distance from an associated processor, which leads to potential for erroneous readings and interference. In addition exposing primary pressure sensor 22 to contamination, such as from blood and to humidity also contribute to potential problems being experienced by primary pressures sensor 22. Backup pressure sensor 26 may be any suitable pressure sensor, including the pressure sensors described above as being suitable as primary pressure sensor 22.

FIG. 2B illustrates an alternative embodiment of the system of FIG. 1 in which an insufflator 110 includes only standard features and is communicatively coupled through a connection 114 to a pressure module 112. Pressure module 112 includes components analogous to those described with respect to FIG. 2A, including a backup pressure sensor 126, but are included in this stand-alone pressure module. Connection 114 between insufflator 110 and pressure module 112 may be wired or wireless. It will be understood that although a software-based system is illustrated in FIGS. 2A and 2B the logic described herein could instead be implemented through hardware circuits or a combination of hardware and software.

Figure 3:
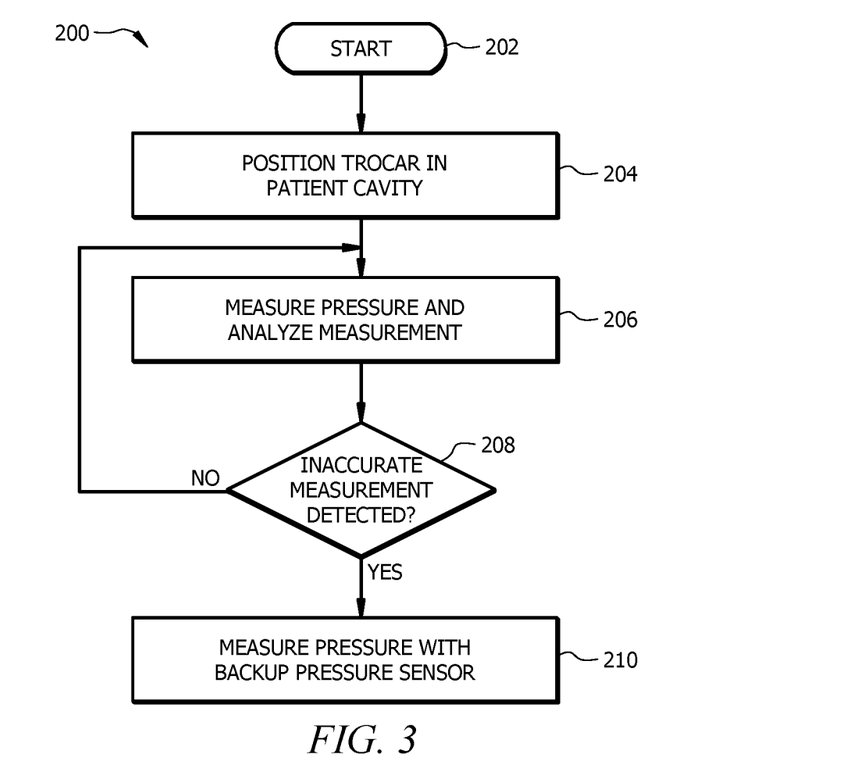
FIG. 3 is a flow chart illustrating a method that includes switching control of an insufflator to be based on pressure measurements of a backup pressure sensor.

FIG. 3 is a flow chart illustrating a method 200 that includes use of a primary pressure sensor and a backup pressure sensor associated with a trocar. The method may utilize structural items such as those described in FIGS. 1A through 2B or may use alternative structural items. Computational steps described below may be performed by any suitable computation device, including insufflator 10 and pressure module 112, for example.

The method begins at step 202.

At step 204, at least a portion of a trocar having a primary pressure sensor is positioned in a patient cavity. The pressure sensor in located on, or associated with, the trocar such that the primary pressure sensor can provide a direct measurement of a pressure in a patient cavity when a portion of the trocar is positioned in the patient cavity. At step 206, the primary pressure sensor repeatedly measures a pressure within the patient cavity and communicates a signal indicative of the measurement to a processor associated with an insufflator. Also at step 206, the processor analyzes the measured pressure for indications of whether the signals indicative of the measured pressure being inaccurate or otherwise suggesting that the primary pressure sensor is operating in a less than optimal manner. Any suitable factors may be considered in such analysis; however, certain factors that may indicate the primary pressure sensor is operating than a less than optimal manner include (1) whether the received signal is not within an expected range for the received signal; (2) whether error data is received, such as whether errors have occurred due to interference from a power signal, the wrong number of bits have been received, data is received in the wrong format, or data is received with improper spacing (3) whether proper acknowledgment bits are not received from the primary pressure sensor, (4) whether the received signal is not within an expected voltage range, (5) whether expected new updated status bits are not received, such as whether a signal has changed enough to indicate a new measurement has occurred as opposed to a signal being so close to a previous signal to indicate no new measurement has occurred; and (6) in the case of two or more pressure sensors located on or near trocar 14, whether measurements by the two or more sensors are not within a certain range of each other.

At step 208, a processor determines, whether the above analysis suggests the primary pressure sensor is not measuring accurately or otherwise not operating in a less than optimal fashion. If not, then processing returns to step 206, and if so, the control by the insufflator is switched to be based on pressure sensed by a backup sensor at step 210.

Although the pressure sensed by a backup pressure sensor 210 is usually not as accurate a measure of the pressure within the patient cavity and as such not as desirable for use in controlling an insufflator associated with a trocar, when problems arise with a primary pressure sensor positioned on or associated with a trocar such the direct pressure measurements within a patient cavity can be made, it can be advantageous to at least temporarily switch control to be based on pressure measurements made by a backup pressure sensor located at the insufflator.

The method concludes at step 212.

Thus, a method and system have been described that uses backup pressure sensor for pressure measurements associated with an insufflator when it is determined that pressure measurements associated with a primary pressure sensor may be inaccurate. By doing so, advantages associated with locating a pressure sensor nearer the patient cavity may be realized.

Although one embodiment has been illustrated and described in detail, it will be understood that various substitutions and alterations can be made therein without departing from the spirit and scope of the present invention, as defined by the following claims. For example, although primary pressure sensor 22 has been described above as being located on trocar 14, primary pressure sensor 22 may be located on, in, or through other medical appliances as well. Such medical appliances may be or include one of: a needle (e.g., veress needle, fistula, Huber, spinal), a stapler, a grasper, a pair of scissors, a scalpel, a cutter, an electrode, an end seal, a probe, a multiple access port, and a single access port. Although this disclosure identifies certain types of medical appliances (including trocars 14), this disclosure recognizes that primary pressure sensor 22 may be located on, in, or through any suitable medical appliance. For example, this disclosure recognizes any medical appliance that can puncture the skin as a medical appliance.

Figure 4:
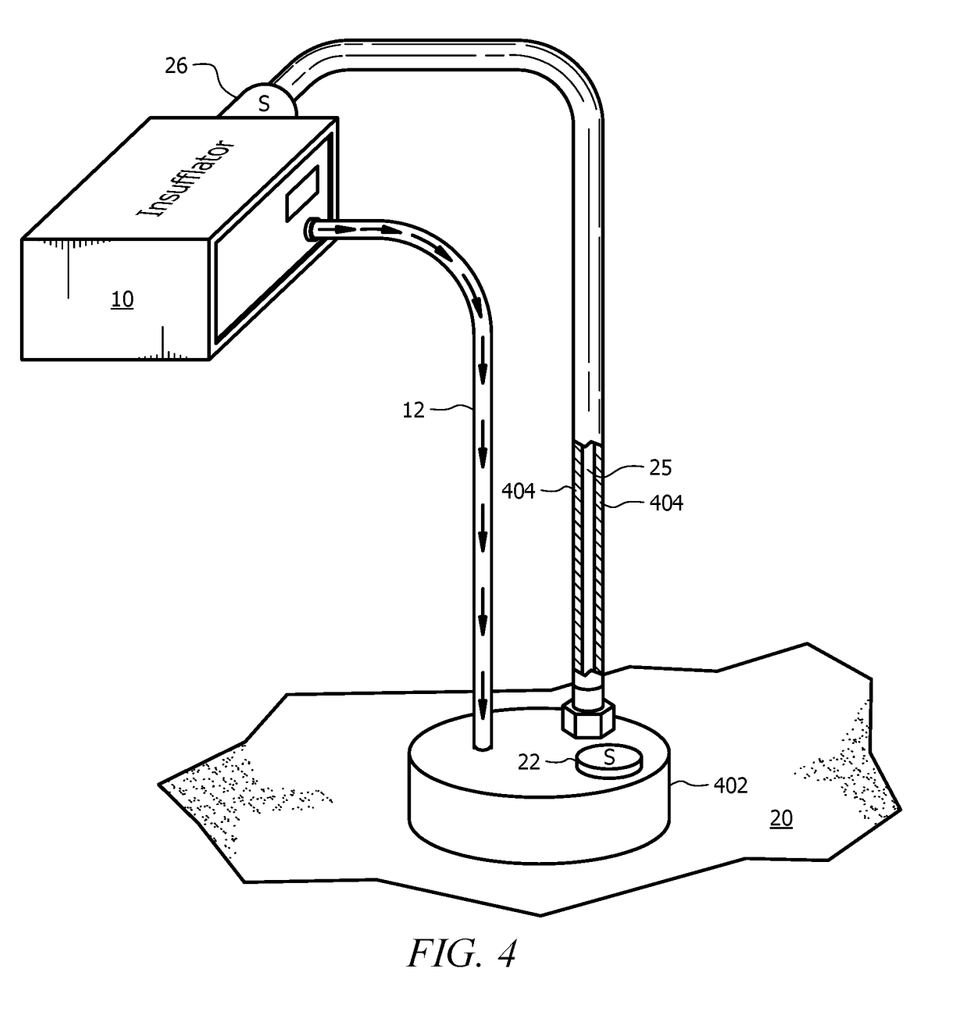
FIG. 4 is a schematic diagram showing a multiple access port having an associated pressure sensor, wherein the multiple access port provides access to the abdominal cavity of a patient.

FIG. 4 illustrates primary pressure sensor 22 being part of or added to a medical port. A medical port may be single access or multiple access. As suggested by their names, a single access port includes one access point by which to introduce fluids and/or medical instruments into a patient and a multiple access port includes more than one access point by which to introduce fluids and/or medical instruments into a patient. FIG. 4 illustrates a particular type of multiple access port known as a GelPort. As will be understood by a person of ordinary skill in the art, a GelPort Laparascopic System generally includes a GelSeal® cap and a wound protector/retractor. The wound protector/retractor is configured to extend through an incision site to patient cavity 20 and the GelSeal® cap provides a seal for the wound protector/retractor. As will also be understood by a person of ordinary skill in the art, GelSeal® cap may comprise a penetrable material that permits the insertion of one or more other medical appliances (e.g., trocar 22, a scalpel, etc.). In some embodiments, through appropriate tubing and/or sleeves, insufflation gas may be introduced into patient cavity 20 and smoke may be removed from patient cavity 20 through GelSeal® cap.

As shown in FIG. 4, only GelSeal® cap 402 of the GelPort is visible. This disclosure recognizes that primary pressure sensor 22 may be included or added onto GelSeal® cap 402 in a manner that permits pressure readings to be taken with respect to patient cavity 20. As discussed above, primary pressure sensor 22 or backup sensor 26 may be coupled to a device (e.g., an insufflator 10, a visual display) via wired connection 25. In some embodiments, wired connection 25 includes sheathing 404 to shield wired connection 25 from electromagnetic frequencies. All of a part of wired connection 25 may be shielded. As illustrated in FIG. 4, wired connection 25 is shielded by sheath 404 and is coupled to backup sensor 26 which provides a backup pressure measurement for primary pressure sensor 22.

What is claimed is:

1. A system comprising:
a medical appliance;
a primary pressure sensor positioned on, in, or through the medical appliance, the primary pressure sensor configured to determine a pressure of a patient cavity;
a backup pressure sensor; and
an insufflator operable to supply insufflation fluid to the patient cavity, the insufflator being communicatively coupled to the primary pressure sensor, the insufflator comprising:
a processor;

a computer-readable media having logic stored thereon, the logic operable, when executed on the processor, to:
- receive one or more signals indicative of pressure measurements from the primary pressure sensor;
- control the supply of the insufflation fluid from the insufflator to the patient cavity based at least on the one or more signals indicative of pressure measurements from the primary pressure sensor; and
- determine that the one or more signals indicative of pressure measurements from the primary pressure sensor may be inaccurate by determining at least one of:
  - whether at least one of the one or more received signals indicative of pressure measurements is not within a predefined range of accuracy;
  - whether any error data is received, the error data indicating at least one of:
    - an error occurred due to an interference from a power signal;
    - a wrong number of bits is received;
    - data is received in a wrong format; or
    - data is received with an improper spacing;
  - whether any proper acknowledgment bits are not received;
  - whether a received signal is not within an expected voltage range; and
  - whether any updated status bits are not received; and
- in response to determining that the one or more signals indicative of pressure measurements from the primary pressure sensor may be inaccurate, control supply of insufflation fluid by the insufflator to the patient cavity based at least on a pressure measured by a backup pressure sensor rather than based on the one or more signals indicative of pressure measurements from the primary pressure sensor.

2. The system of claim 1, wherein the medical appliance is a trocar.

3. The system of claim 1, wherein the medical appliance is one of:
- a needle;
- a stapler;
- a grasper;
- a pair of scissors;
- a scalpel;
- a cutter;
- an electrode; and
- an end seal.

4. The system of claim 1, wherein the medical appliance is one of:
- a multiple access port; and
- a single access port.

5. The system of claim 1, wherein the insufflation fluid is a gas that is supplied to the patient cavity through the medical appliance.

6. The system of claim 1, wherein the backup pressure sensor is located at one of:
- in, on, or through the medical appliance; and
- within the insufflator.

7. The system of claim 1, wherein:
- at least one of the primary pressure sensor or the backup pressure sensor is coupled to a cable;
- at least a portion of the cable is shielded from electromagnetic frequencies.

8. The system of claim 1, wherein the insufflator receives the one or more signals indicative of pressure measurements from the primary pressure sensor when the primary pressure sensor is positioned at or within a patient incision site.

9. A method comprising:
- positioning a medical appliance having a primary pressure sensor at or within a patient incision site;
- supplying an insufflation fluid to a patient cavity;
- a receiving one or more signals indicative of pressure measurements in the patient cavity by the primary pressure sensor;
- controlling the supply of insufflation fluid by an insufflator to the patient cavity based at least on the one or more signals indicative of pressure measurements;
- determining, by a processor associated with the insufflator, that the one or more signals indicative of pressure measurements may be inaccurate by determining at least one of:
  - whether at least one of the one or more of the received signals indicative of pressure measurements is not within a predefined range of accuracy;
  - whether any error data is received, the error data indicating at least one of:
    - an error occurred due to an interference from a power signal;
    - a wrong number of bits is received;
    - data is received in a wrong format; or
    - data is received with an improper spacing;
  - whether any proper acknowledgment bits are not received;
  - whether a received signal is not within an expected voltage range; and
  - whether any updated status bits are not received; and
- in response to determining that the one or more signals indicative of pressure measurements may be inaccurate, controlling, by the insufflator, the supply of the insufflation fluid to the patient cavity based at least on a pressure measured by a backup pressure sensor.

10. The method of claim 9, wherein the medical appliance is a trocar.

11. The method of claim 9, wherein the medical appliance is one of:
- a needle;
- a stapler;
- a grasper;
- a pair of scissors;
- a scalpel;
- a cutter;
- an electrode; and
- an end seal.

12. The method of claim 9, wherein the medical appliance is one of:
- a multiple access port; and
- a single access port.

13. The method of claim 9, wherein the backup pressure sensor is located in, on, or through the medical appliance.

14. The method of claim 9, wherein the backup pressure sensor is located within the insufflator.

15. An insufflator comprising:
- a pressurized fluid source;
- a processor; and
- a computer-readable media having logic stored thereon, the logic operable, when executed on the processor, to:
  - receive one or more signals indicative of pressure measurements from a primary pressure sensor positioned on, in, or through a medical appliance, wherein:

the medical appliance is positioned at or within a patient cavity; and the one or more received signals are indicative of a pressure of the patient cavity;

control a supply of insufflation fluid from the pressurized fluid source to the patient cavity based at least on the one or more signals indicative of pressure measurements from the primary pressure sensor; and determining that the one or more signals indicative of pressure measurements from the primary pressure sensor may be inaccurate by determining at least one of:

whether at least one of the one or more received signals indicative of pressure measurements is not within a predefined range of accuracy;

whether any error data is received, the error data indicating at least one of:
  an error occurred due to an interference from a power signal;
  a wrong number of bits is received;
  data is received in a wrong format; or
  data is received with an improper spacing;

whether any proper acknowledgment bits are not received;

whether a received signal is not within an expected voltage range; and whether any updated status bits are not received; and in response to determining that the one or more signals indicative of pressure measurements from the primary pressure sensor may be inaccurate, control the supply of the insufflation fluid by the pressurized fluid source to the patient cavity based at least on a pressure measured by a backup pressure sensor.

16. The insufflator of claim 15, wherein the medical appliance is a trocar.

17. The insufflator of claim 16, wherein the medial appliance is one of:
  a needle;
  a stapler;
  a grasper;
  a pair of scissors;
  a scalpel;
  a cutter;
  an electrode;
  an end seal;
  a multiple access port; and
  a single access port.

18. A computer-readable media having logic stored thereon, the logic operable, when executed on a processor, to:

receive one or more signals indicative of pressure measurements from a primary pressure sensor positioned on, in, or through a medical appliance, the medical appliance being positioned at or within a patient incision site;

control a supply of insufflation fluid to the patient cavity based at least on the one or more received signals indicative of pressure measurements from the primary pressure sensor; and determining that the one or more signals indicative of pressure measurements from the primary pressure sensor may be inaccurate by determining at least one of:
  by determining at least one of:
  whether at least one of the one or more received signals indicative of pressure measurements is not within a predefined range of accuracy;
  whether any error data is received, the error data indicating at least one of:
    an error occurred due to an interference from a power signal;
    a wrong number of bits is received;
    data is received in a wrong format; or
    data is received with an improper spacing;
  whether any proper acknowledgment bits are not received;
  whether a received signal is not within an expected voltage range; and
  whether any updated status bits are not received; and
  in response to determining that the one or more signals indicative of pressure measurements from the primary pressure sensor may be inaccurate, control the supply of insufflation fluid to the patient cavity based at least on a pressure measured by a backup pressure sensor.

19. The computer-readable media claim 18, wherein the medical appliance is a trocar.

20. The computer-readable media claim 18, wherein the medial appliance is one of:
  a needle;
  a stapler;
  a grasper;
  a pair of scissors;
  a scalpel;
  a cutter;
  an electrode;
  an end seal;
  a GelPort; and
  a single access port.

* * * * *